(12) United States Patent
Griffin et al.

(10) Patent No.: US 9,034,280 B2
(45) Date of Patent: May 19, 2015

(54) HIGH-THROUGHPUT METHODS AND SYSTEMS FOR PROCESSING BIOLOGICAL MATERIALS

(75) Inventors: Weston Blaine Griffin, Niskayuna, NY (US); Jaydeep Roy, Saratoga Springs, NY (US); Phillip Alexander Shoemaker, Scotia, NY (US); William Patrick Waters, Scotia, NY (US)

(73) Assignee: GENERAL ELECTRIC CORPORATION, Niskayuna, NY (US)

( * ) Notice: Subject to any disclaimer, the term of this patent is extended or adjusted under 35 U.S.C. 154(b) by 866 days.

(21) Appl. No.: 12/639,479

(22) Filed: Dec. 16, 2009

(65) Prior Publication Data

US 2011/0143427 A1 Jun. 16, 2011

(51) Int. Cl.
*B01L 3/00* (2006.01)
*A61M 1/02* (2006.01)
*B01D 21/26* (2006.01)
*B03D 3/00* (2006.01)

(52) U.S. Cl.
CPC .............. *A61M 1/0209* (2013.01); *B01D 21/26* (2013.01); *B03D 3/00* (2013.01)

(58) Field of Classification Search
CPC .................................................. A61M 1/0209
USPC ................................................. 422/554, 551
See application file for complete search history.

(56) References Cited

U.S. PATENT DOCUMENTS

| | | | |
|---|---|---|---|
| 3,954,323 A | 5/1976 | Andrews et al. | |
| 4,038,194 A | 7/1977 | Luceyk et al. | |
| 4,663,058 A | 5/1987 | Wells et al. | |
| 4,889,524 A | 12/1989 | Fell et al. | |
| 5,174,894 A | 12/1992 | Ohsawa et al. | |
| 5,387,187 A | 2/1995 | Fell et al. | |
| 5,789,147 A | 8/1998 | Rubinstein et al. | |
| 6,123,655 A | 9/2000 | Fell | |
| 6,325,775 B1 | 12/2001 | Thom et al. | |
| 6,391,541 B1 | 5/2002 | Petersen et al. | |
| 6,406,919 B1 | 6/2002 | Tyrrell | |
| 6,471,855 B1 | 10/2002 | Odak et al. | |
| 6,544,751 B1 | 4/2003 | Brandwein et al. | |
| 6,582,386 B2 | 6/2003 | Min et al. | |
| 6,673,627 B2 | 1/2004 | Tyrrell et al. | |
| 6,695,803 B1 * | 2/2004 | Robinson et al. ............ 604/4.01 |
| 6,733,433 B1 | 5/2004 | Fell | |
| 6,759,007 B1 | 7/2004 | Westberg et al. | |
| 7,001,513 B2 | 2/2006 | Bell | |
| 7,211,191 B2 | 5/2007 | Coelho et al. | |
| 7,241,281 B2 | 7/2007 | Coelho et al. | |
| 2002/0020680 A1 | 2/2002 | Jorgensen | |
| 2002/0179537 A1 | 12/2002 | Sukavaneshvar et al. | |
| 2002/0188263 A1 | 12/2002 | Le Bui et al. | |
| 2003/0134416 A1 | 7/2003 | Yamanishi et al. | |
| 2004/0023399 A1 | 2/2004 | Grzeda et al. | |
| 2004/0079688 A1 | 4/2004 | Muller | |
| 2004/0127841 A1 | 7/2004 | Briggs | |
| 2005/0029181 A1 | 2/2005 | Bell | |
| 2005/0137516 A1 | 6/2005 | Min et al. | |
| 2008/0090406 A1 | 4/2008 | Jensen | |
| 2008/0171951 A1 | 7/2008 | Fell | |
| 2009/0299272 A1 | 12/2009 | Hopping et al. | |

FOREIGN PATENT DOCUMENTS

| | | |
|---|---|---|
| WO | 9623872 | 8/1996 |
| WO | 9705938 | 2/1997 |
| WO | 0038762 | 7/2000 |
| WO | 03009889 A1 | 2/2003 |
| WO | 2006100651 A1 | 9/2006 |
| WO | 2006120415 A1 | 11/2006 |

OTHER PUBLICATIONS

International Search Report mailed May 18, 2011 for International Application No. PCT/EP2010/069711.

* cited by examiner

*Primary Examiner* — Natalia Levkovich
(74) *Attorney, Agent, or Firm* — Fletcher Yoder, P.C.

(57) ABSTRACT

A high-throughput system for processing biological material that comprises: a tray that supports a functionally-closed fluid path subsystem comprising, a vessel for containing and enabling the biological material to separate into two or more distinct submaterials; one or more receptacles to receive one or more of the submaterials from the vessel; a filtration device; a conduit through which one or more submaterials are transported between at least the vessel and the filtration device; and a first engagement structure; a processing unit comprising, a pumping device for moving one or more of the submaterials between at least the vessel and the filtration device via the conduit; a second engagement structure corresponding to the first engagement structure; a locking mechanism for at least temporarily holding the tray in a fixed position relative to the processing unit; a control device that automatically starts and stops the pumping device in response to one or more commands.

34 Claims, 15 Drawing Sheets

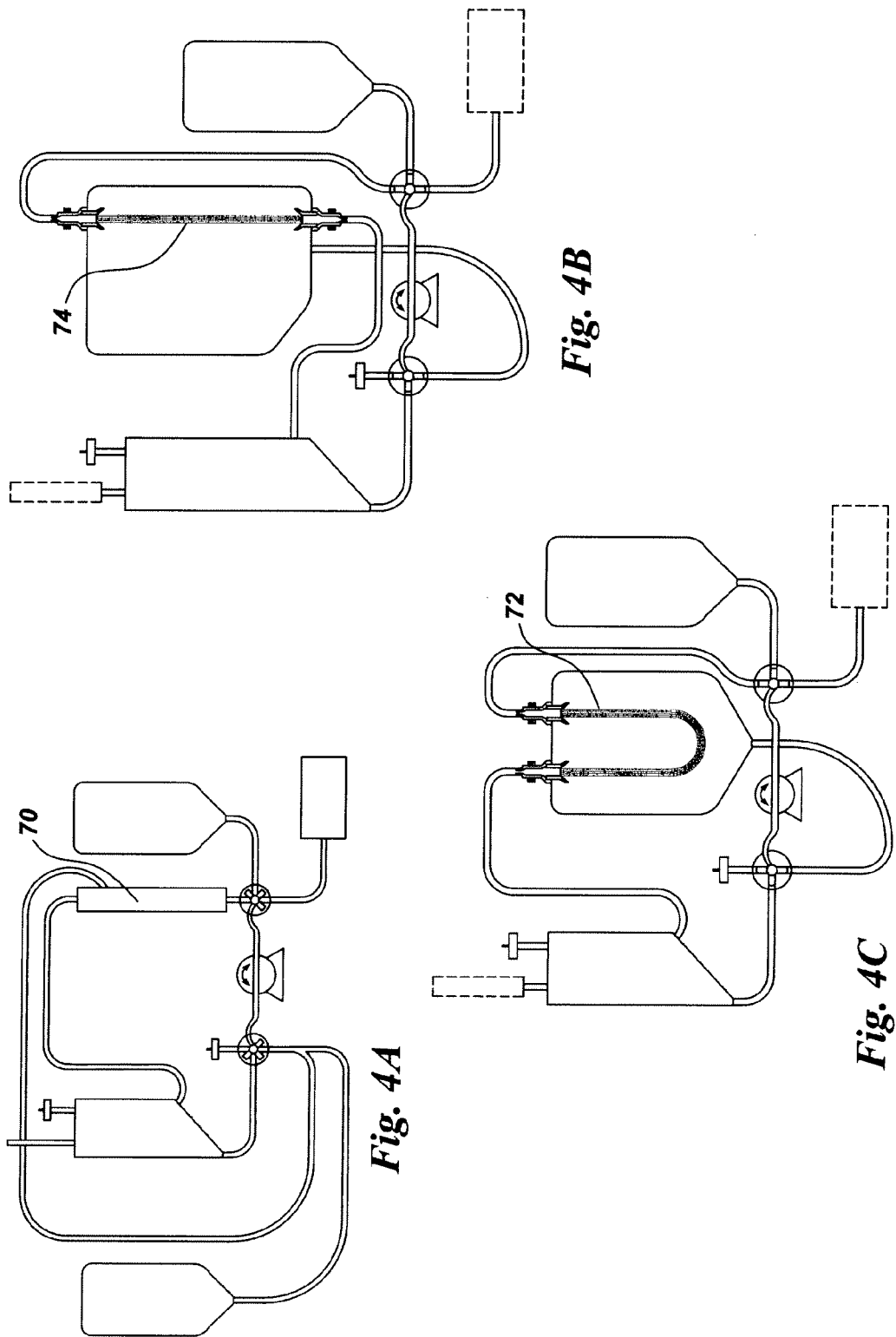

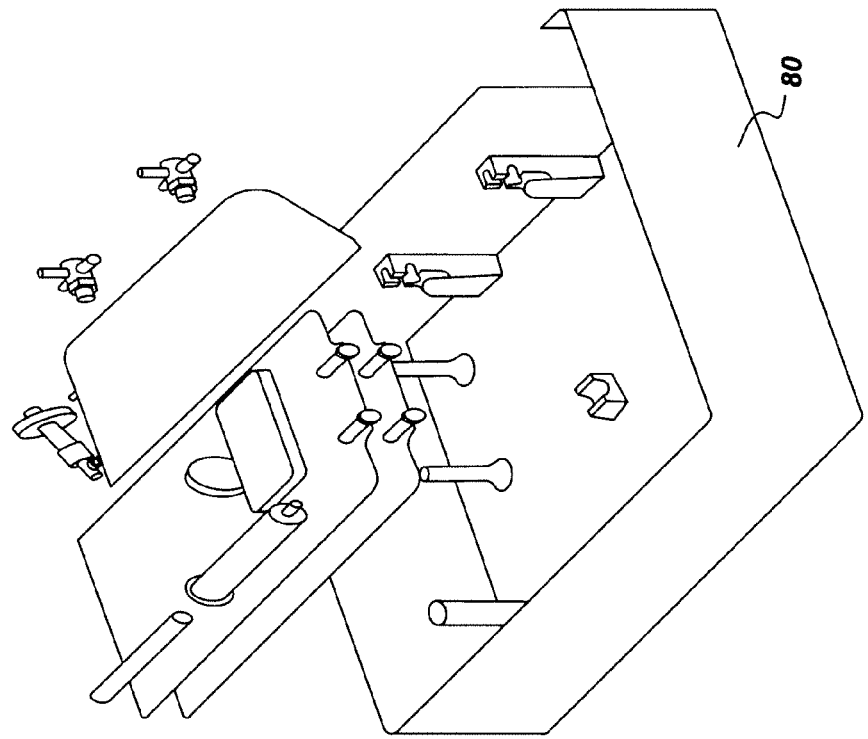
Fig. 5A
Fig. 5B
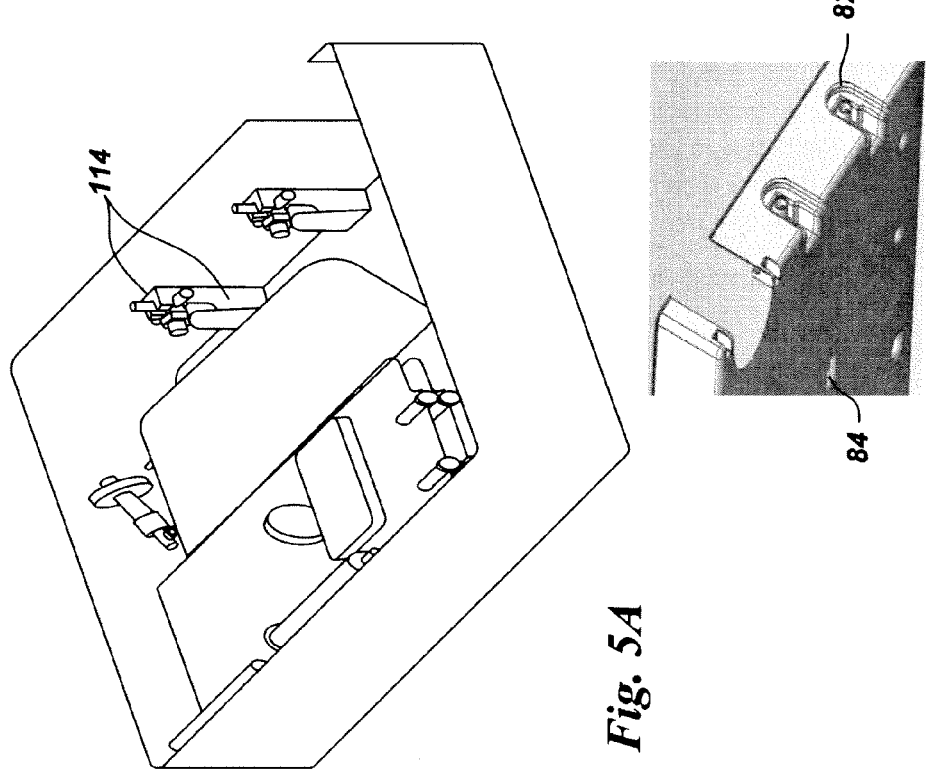
Fig. 5C

HIGH-THROUGHPUT METHODS AND SYSTEMS FOR PROCESSING BIOLOGICAL MATERIALS

BACKGROUND

The invention relates generally to automated systems with high-throughput cassettes, for processing complex biological materials into subcomponents.

Many conventional blood cell isolation procedures require preliminary red blood cell depletion and sample volume reduction. These are commonly required processing steps for long-term cell banking and regenerative medicine applications where a maximal yield of rare cells is desired in a reduced volume due to storage limitations and/or the small volume requirements needed for direct transplantation. Today, the most common techniques for processing blood-cell containing samples (e.g. cord blood, bone marrow, peripheral blood) involve density-gradient sedimentation using centrifugation with or without the use of a density-gradient media to improve separations. Automated centrifugal based systems have recently been developed for closed-system processing of cord blood and bone marrow samples in order to meet the growing needs for high-throughput sample processing. While greatly improving throughput compared to manual techniques, centrifugation-based devices have limited flexibility and portability due to the weight and fixed physical dimensions of the centrifuge bucket.

These techniques and devices are also associated with low sample throughput and tedious manual operation. The current centrifuge based systems require labor-intensive pre-processing set-up. For example, the operator must route or otherwise load the tubing and position parts in a very confined space within the centrifuge-based device. This approach tends to result in sample leakage and device failure due to kinked tubing and improper installation.

BRIEF DESCRIPTION

One or more embodiments of the methods and systems address the need for a functionally closed and sterile high throughput system for processing biological materials, such as whole blood, while achieving high target cell (such as stem cell) recoveries and viabilities for downstream cell therapy applications. One or more embodiments of the system may be configured to operate synchronously or asynchronously.

The biological materials may be added to a specialized disposable processing set through a sterile or aseptic method. The processing set is optimized to function with a machine to manipulate the biological materials towards some end, such as, target cell isolation and/or sample concentration. To achieve high throughput sample processing, the cell processing system may be optimized for fast sample processing while maintaining end-goal specifications for recovery. With the increase complexity of the disposable processing sets, technician time for preparation and loading can have a significant impact on throughput capability. One or more embodiments of the system of the invention offer the advantages of a ready-to-ship package (containing the disposable processing set) with features that enable easy loading of the disposable into the machine. As such, the systems minimize technician preparation and loading time, and also provide features that allow the associated machine to interact with the disposable components of the systems.

Various embodiments of the systems provide a simplified fluid-path (e.g. reduces disposable cost and dead volumes, and improves cell recovery potential); make use of a disposable tray and mating hard cassette for placement and operation of sterile disposable set, which in part reduces the number of manual steps and substantially decrease the operator time; and enable the asynchronous but parallel operation of multiple-channels within one automation system (e.g. to improve sample throughput). An embodiment of a high-throughput system of the invention for processing biological material comprises: a tray that supports a functionally-closed fluid path subsystem comprising, a vessel for containing and enabling the biological material to separate into two or more distinct submaterials; one or more receptacles to receive one or more of the submaterials from the vessel; a filtration device; a conduit through which one or more submaterials are transported between at least the vessel and the filtration device; and a first engagement structure; a processing unit comprising, a pumping device for moving one or more of the submaterials between at least the vessel and the filtration device via the conduit; a second engagement structure corresponding to the first engagement structure; a locking mechanism for at least temporarily holding the tray in a fixed position relative to the processing unit; a control device that automatically starts and stops the pumping device in response to one or more commands. One of the receptacles may comprise, but are not limited to, a supply receptacle (e.g. for a reagent), a waste filtrate receptacle and a target retentate receptacle.

The first engagement structure may comprise one or more valves in fluid communication with the conduit for selectively directing the material or one or more submaterials between one or more of: the vessel, the filtration device, and the receptacles, and wherein the control device automatically opens and closes the valve. The pumping device may be configured to contact the conduit intermittently, to facilitate the movement of the material or one or more submaterials between one or more of: the vessel, the filtration device, and the receptacles, wherein the pumping device comprises a plurality of spaced contact points, at least one of which is in contact with the conduit at any given moment when the pump is in operation.

The system may further comprise a shoe that corresponds to the pumping device, between which a portion of the conduit is positioned, wherein the shoe has a curved surface that corresponds to a curved surface of the pumping device. The pumping device may comprise a rotating circular component having a perimeter about which a plurality of spaced contact points are located, at least one of which is in contact with the conduit at any given moment when the pump head engages the shoe. For example, the circular component may comprise three contact points that are located substantially equidistant from each other about the perimeter.

The system may further comprise a cassette adapted to support the tray in a substantially fixed position relative to the processing unit, wherein the shoe is located in the cassette. The cassette may comprise one or more surface features that mate with one or more corresponding surface features in the tray to hold one or more of the tray, the vessel, one or more of the receptacles, the conduit or combinations thereof, in a substantially fixed position relative to the housing unit. The system may further comprise a sensor for sensing one or more characteristics of the materials or submaterials, wherein at least one of the surface features of the cassette hold at least a portion of the vessel in a position relative to the sensor, and wherein the sensor is located in the housing unit.

The first engagement structure of the fluid path subsystem may comprise one or more valves in fluid communication with the conduit for selectively directing the material or one or more submaterials between one or more of: the vessel, the filtration device, and the receptacles; wherein the second engagement structure of the processing unit comprises a drive assembly; and wherein the control device automatically controls the drive subsystem to open and close the valves.

The locking mechanism of the system may comprise one or more alignment components that align the tray with the processing unit along an x, y and z axes, wherein one or more of the alignment components may comprise, but are not limited to, a pin and corresponding bore.

The first engagement structure and the second engagement structure may comprise corresponding dovetail features, wherein the first and second engagement structures are configured to compensate for small mating misalignments in position, and wherein the control system comprises a feature to compensate for any backlash between the valve and the drive assembly and a homing feature to adjust a position of the valve of the first engagement structure relative to a reference point.

The processing unit may comprise a plurality of guides, to support and position a corresponding number of trays in the housing unit, wherein a plurality of fluid path subsystems may be configured to operate asynchronously.

Another embodiment of an automated high-throughput system of the invention, for processing biological material, that is adapted to work in conjunction with a functionally closed fluid path subsystem that is supported by a tray and comprises, a vessel for containing and enabling the biological material to separate into two or more distinct submaterials, one or more receptacles to receive one or more of the submaterials from the vessel, a filtration device, a conduit through which one or more submaterials are transported between the vessel and the filtration device, and a first engagement structure, comprises: a processing unit comprising, a pumping device for moving one or more of the submaterials between at least the vessel and the filtration device via the conduit; and a second engagement structure corresponding to the first engagement structure, a locking mechanism to at least temporarily hold the support structure in a fixed position relative to the processing unit; and a control device that automatically turns the pumping device on and off in response to one or more commands.

The pumping device may be configured to contact the conduit intermittently, to facilitate the movement of the material or one or more submaterials between one or more of: the vessel, the filtration device, and the receptacles, wherein the pumping device comprises a plurality of spaced contact points, at least one of which is in contact with the conduit at any given moment when the pump is in operation. The system may further comprise a shoe that has a curved surface that corresponds to a curved surface of the pumping device, between which a portion of the conduit is positioned. The pumping device may comprise a rotating circular component having a perimeter about which a plurality of spaced contact points are located substantially equidistant from each other about the perimeter, at least one of which is in contact with the conduit at any given moment when the pump is in operation.

The system may further comprise a cassette adapted to support the tray in a substantially fixed position relative to the processing unit, wherein the shoe is located in the cassette. The cassette may comprises one or more surface features that mate with one or more corresponding surface features in the tray to hold one or more of the tray, the vessel, one or more of the receptacles, the conduit or combinations thereof, in a substantially fixed position relative to the processing unit. The system may further comprise one or more sensors for sensing one or more characteristics of the materials or submaterials, wherein at least one of the surface features of the tray hold at least a portion of the vessel in a position relative to the sensor.

The first engagement structure of this embodiment may comprise a valve, and the second engagement structure comprises a drive assembly and is configured to compensate for small mating misalignments in position. The control system may also comprise a feature to compensate for any backlash between the valve and the drive assembly and a homing feature to determine a position of the valve relative to a reference point.

An example of a high-throughput method of the invention, for processing biological material, comprises: a) connecting a source containing the biological material to a port in fluid communication with a functionally closed fluid path subsystem, housed in a tray, the subsystem comprising, at least one first engagement device, at least one valve with one or more ports, a vessel for containing and enabling the biological material to separate into two or more distinct submaterials, one or more receptacles to receive one or more of the submaterials from the vessel, a filtration device, and a conduit through which one or more submaterials are transported between the vessel and the filtration device; b) placing the tray in a cassette; c) inserting the cassette into a processing unit comprising, a pumping device for moving one or more of the submaterials at least between the vessel and the filtration device via the conduit; one or more second engagement structures corresponding to the first engagement structures for opening and closing the valve ports; and a locking mechanism to at least temporarily hold the cassette in a fixed position relative to the processing unit; d) engaging the first engagement structure with the second engagement structure; and e) activating a control device that automatically starts and stops the pumping device, automatically opens and closes the valve ports, to move the biological material through the fluid path subsystem. The method may further comprise, asynchronously repeating steps a) through e) for one or more additional sources of biological materials, connecting each source with a separate additional tray and cassette.

Unlike current methods, the methods and systems of the invention enable automated processing of complex biological materials without requiring users to purchase and use a separate centrifuge. The methods and systems of the invention are also readily adaptable to handle a range of starting volumes, to concentrate a sample to a user-specified final volume, and for use in multiplexing processes (e.g. increasing/decreasing number of samples processed/run).

DRAWINGS

These and other features, aspects, and advantages of the present invention will become better understood when the following detailed description is read with reference to the accompanying drawings in which like characters represent like parts throughout the drawings, wherein.

Figure 6B:
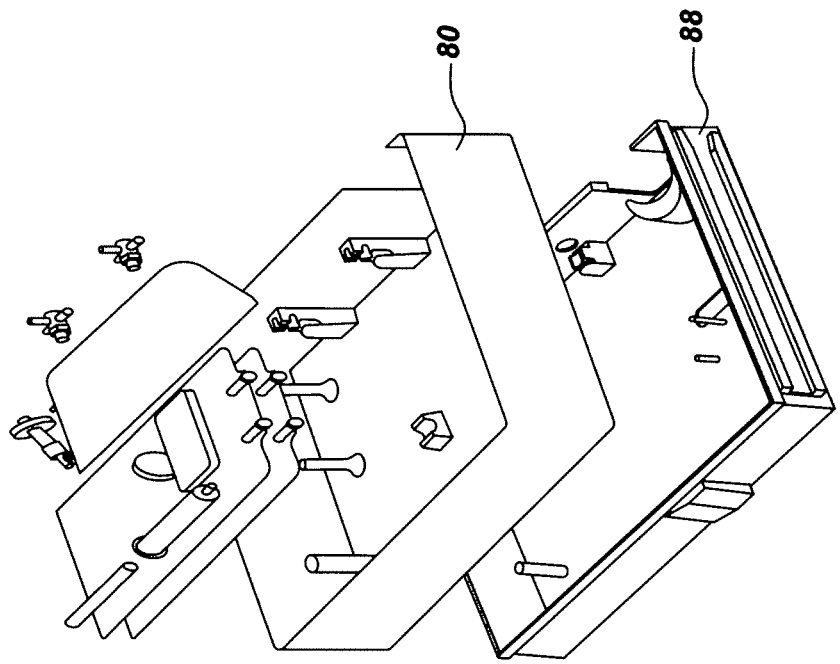
Figure 6A:
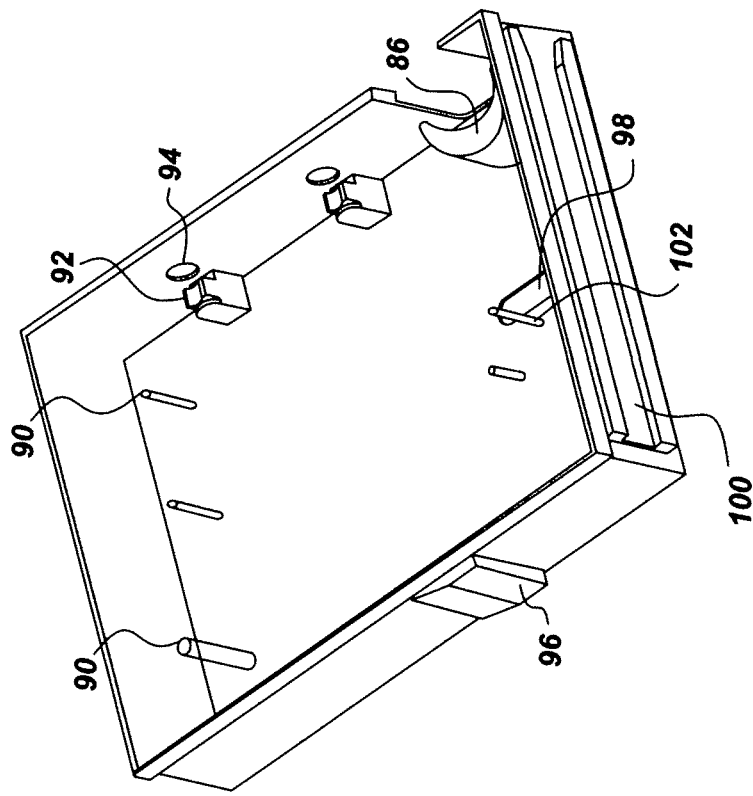
Figure 7:
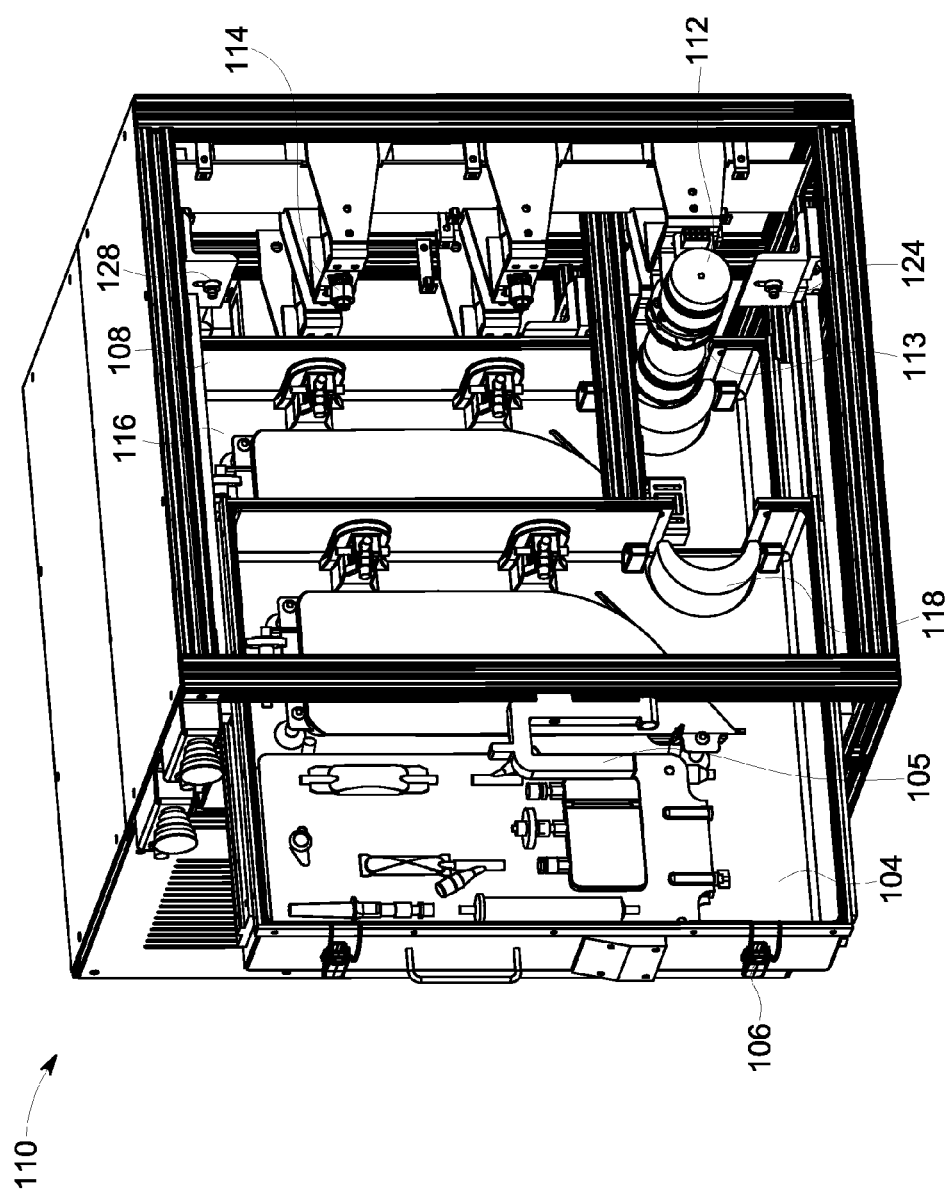
Figure 8A:
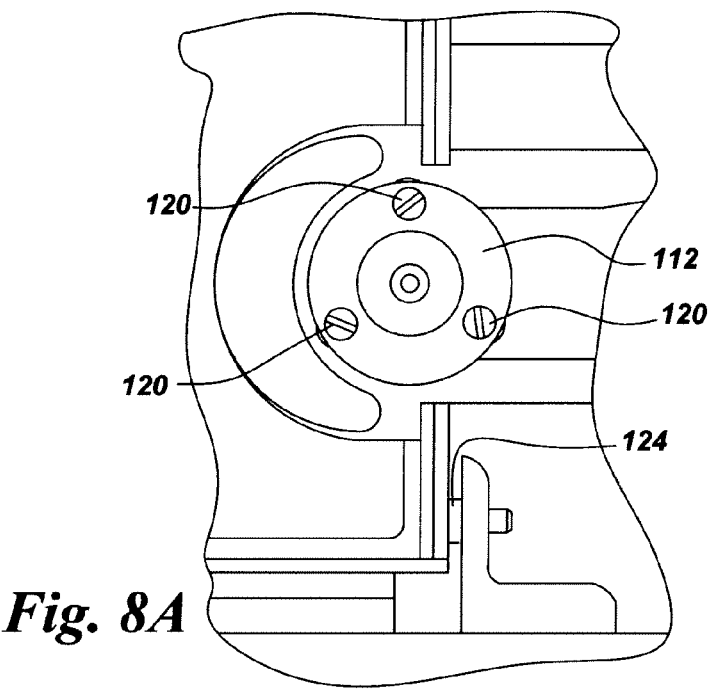
Figure 8B:
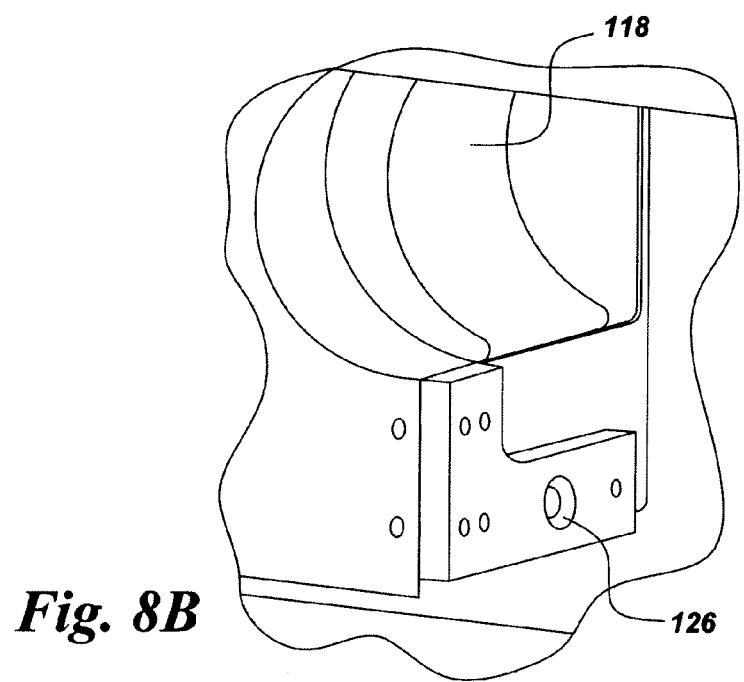
Figure 9A:
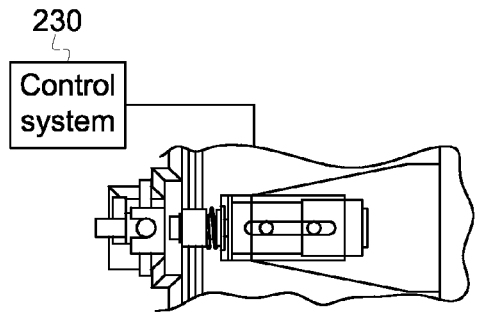
Figure 9B:
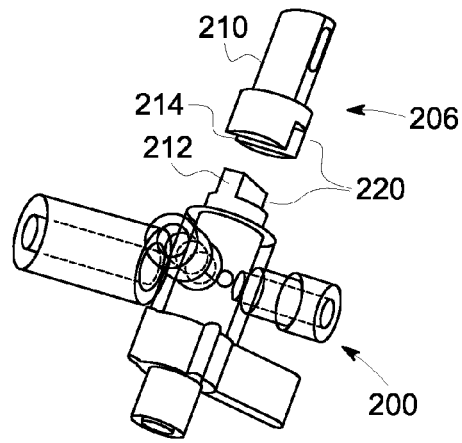
Figure 9C:
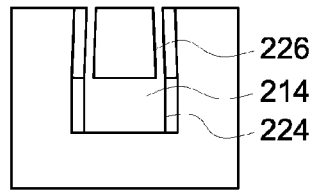
Figure 9D:
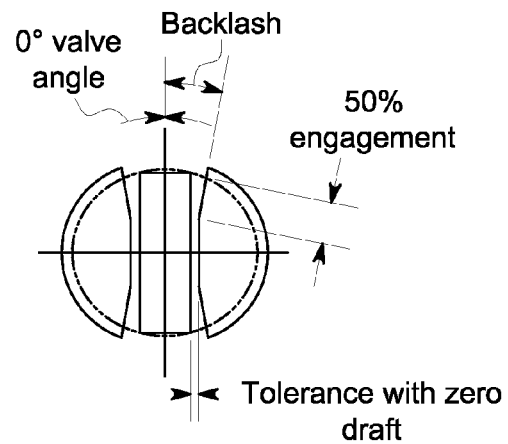
Figure 9E:
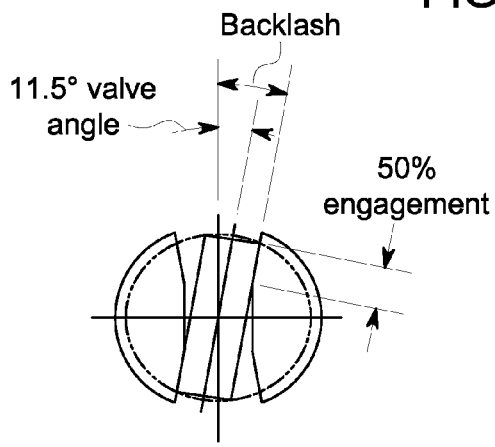
Figure 10A:
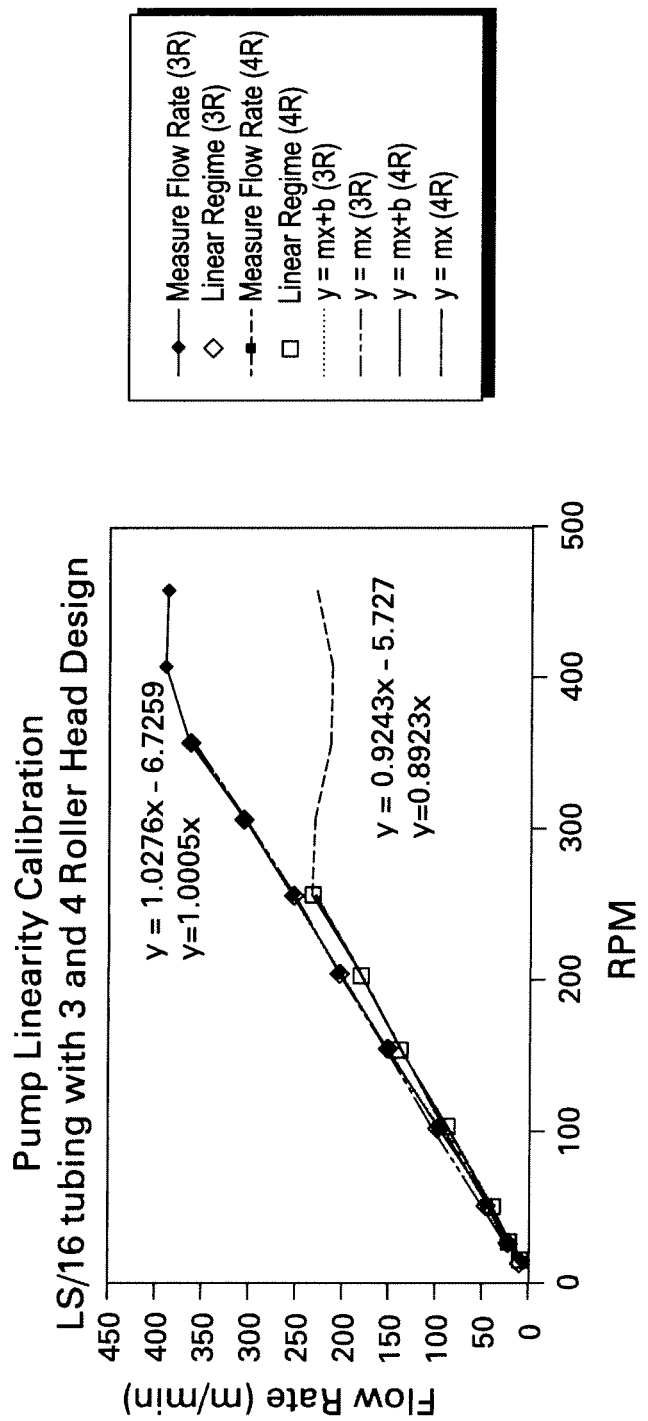
Figure 10B:
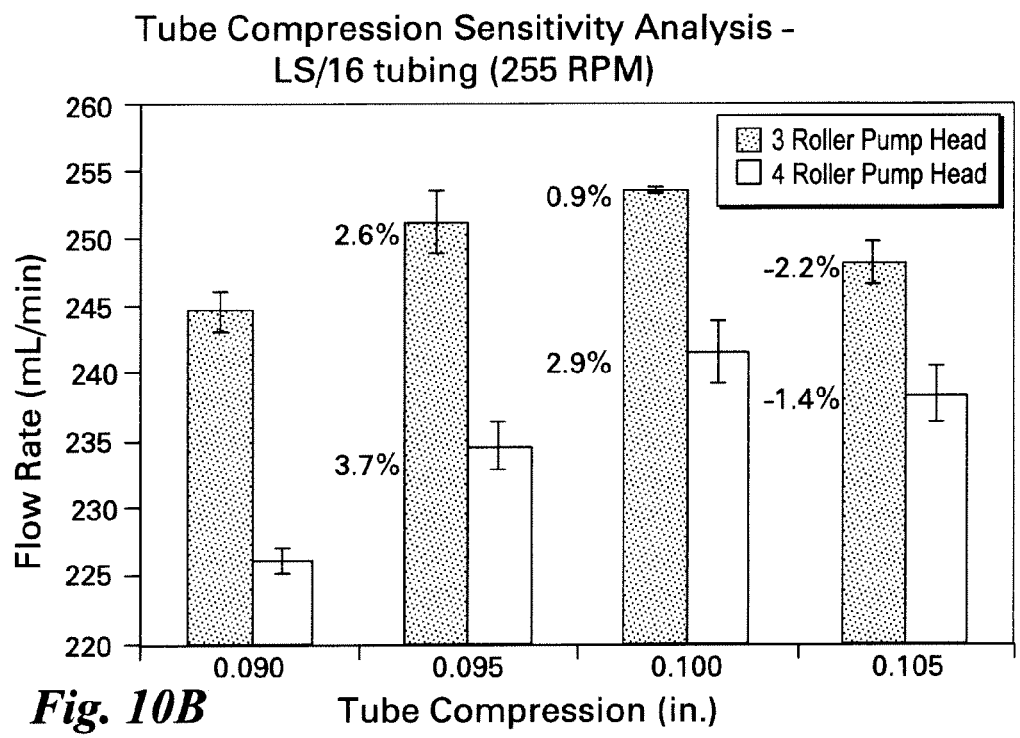
Figure 10C:
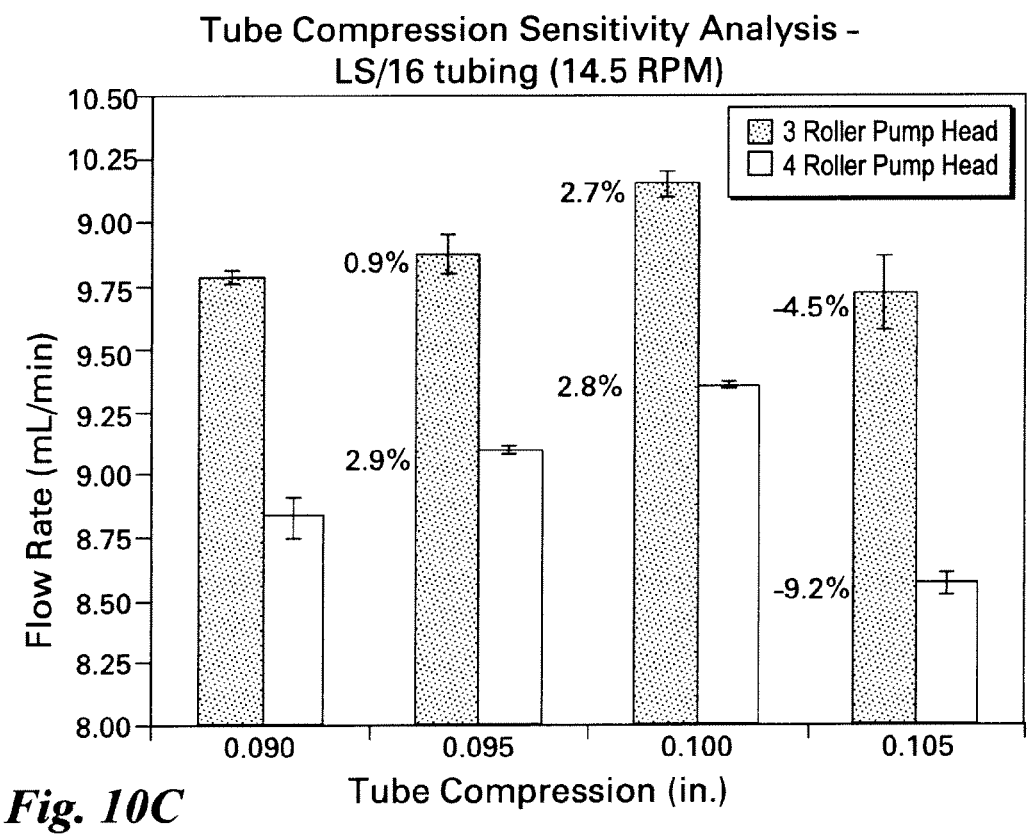
Figure 11A:
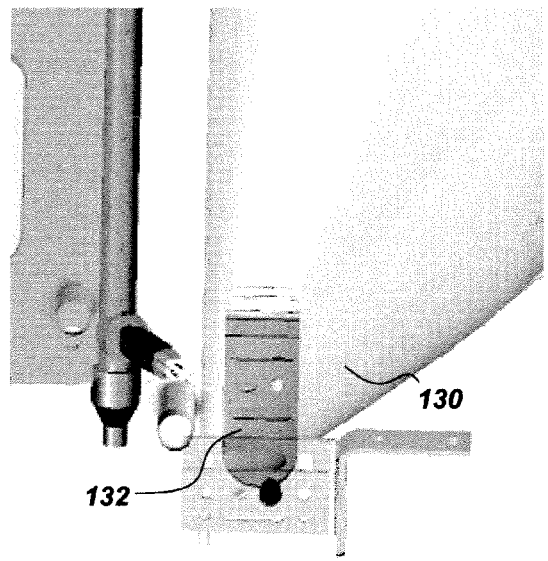
Figure 11B:
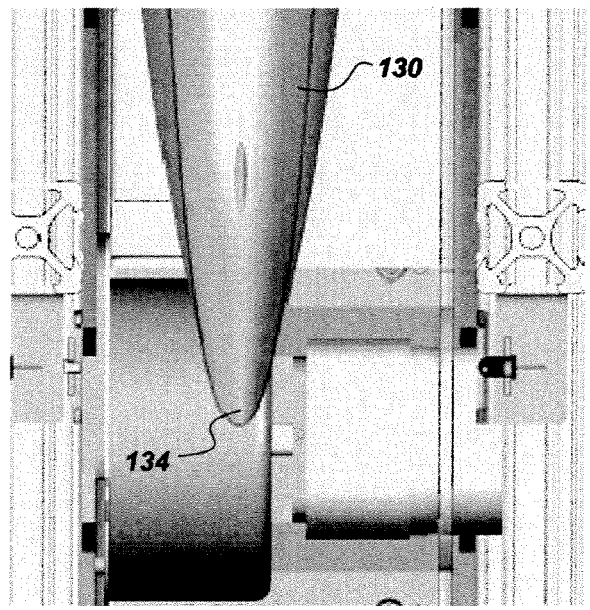
Figure 12A:
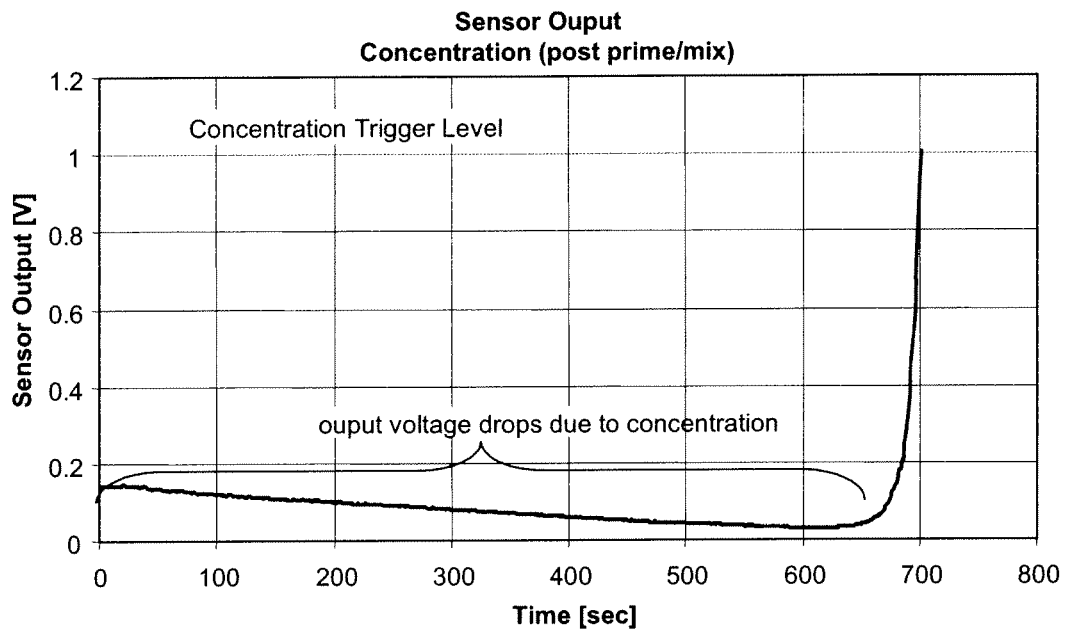
Figure 12B:
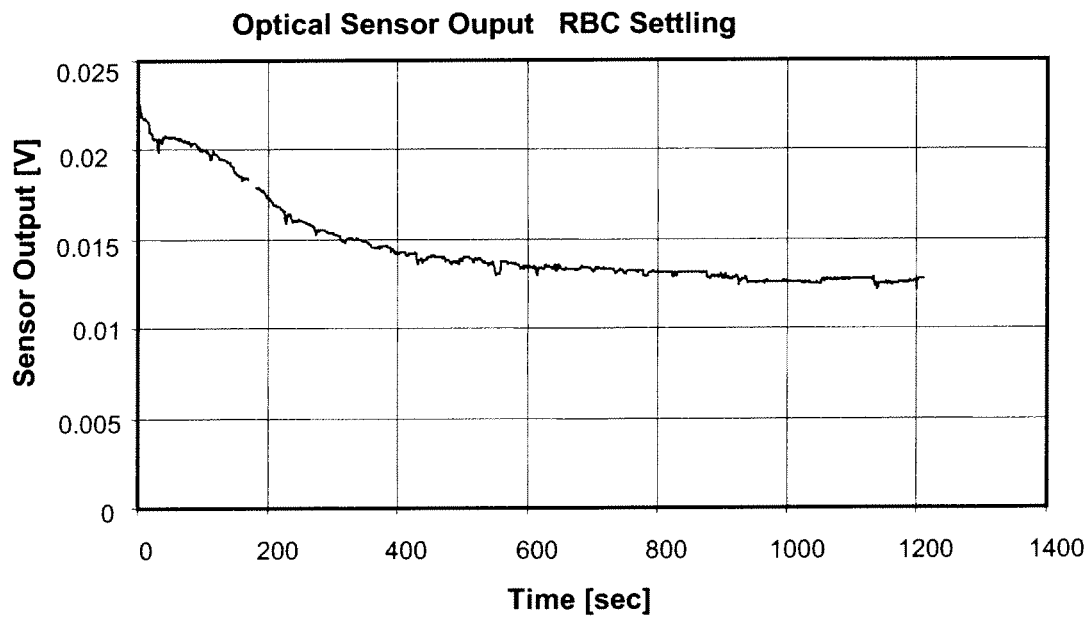
Figure 12C:
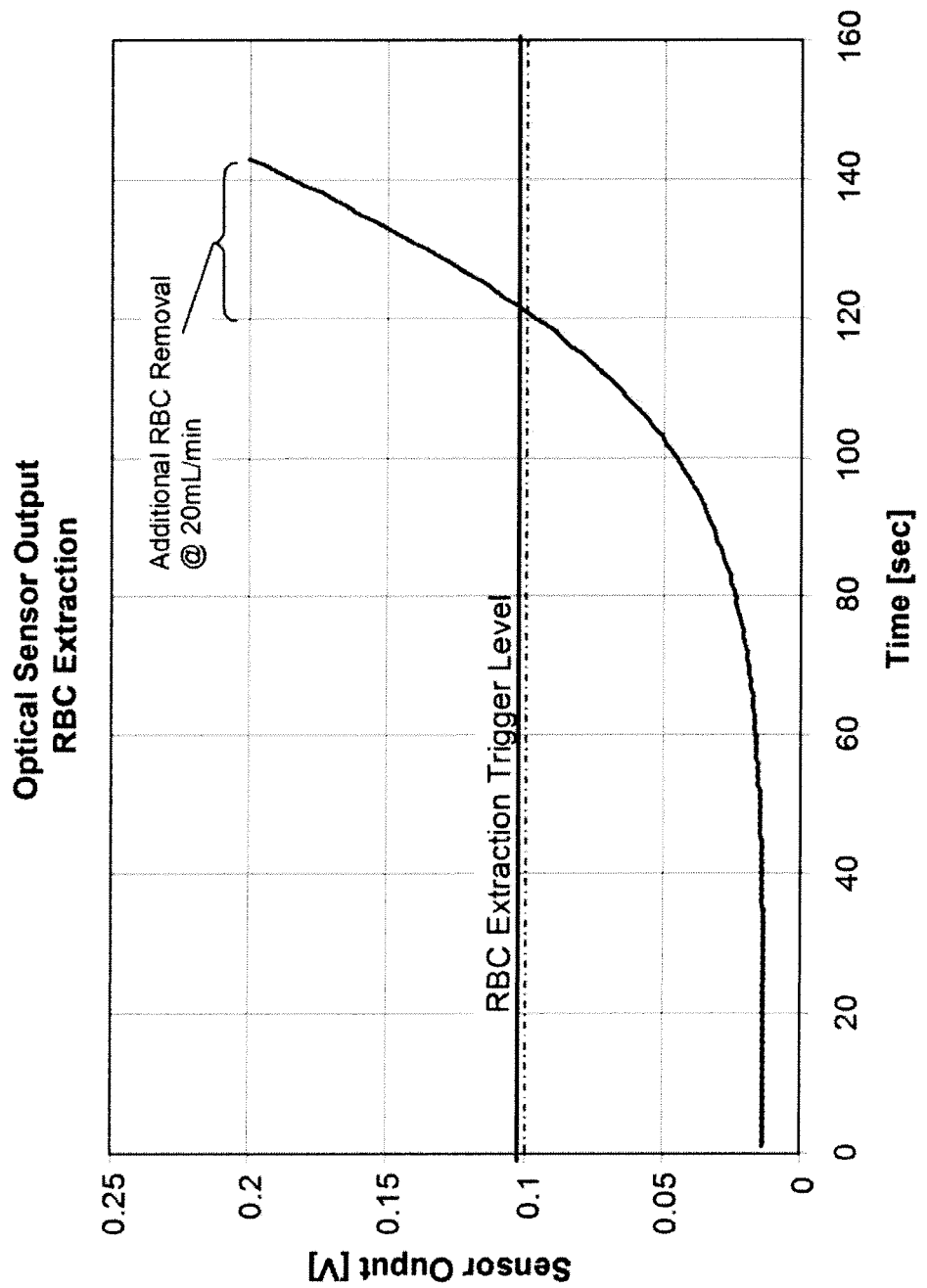
Figure 13:
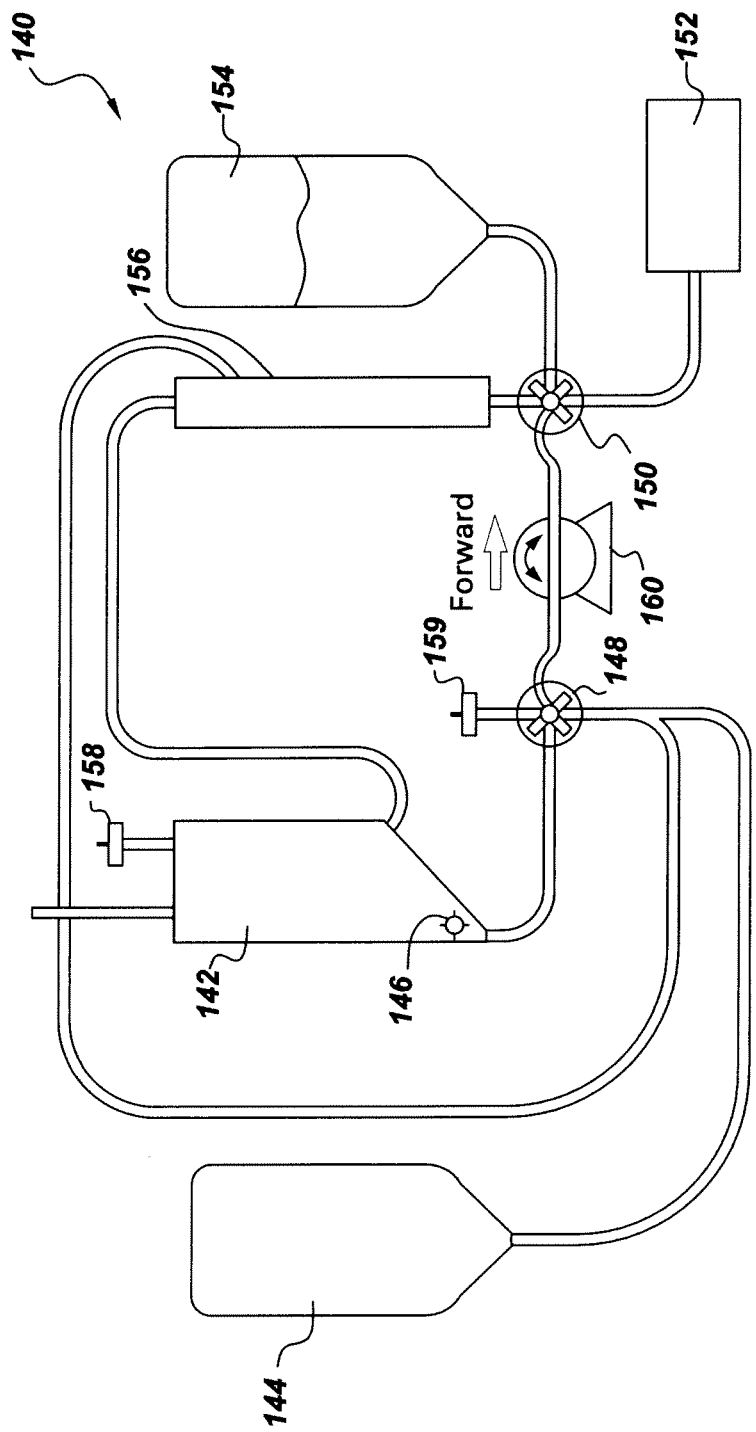

FIGS. 4A-4C are schematic drawings of three embodiments of the filter device incorporated into the functionally closed system of the tray, each drawing also illustrating the position of an embodiment of a pump of the processing unit relative to the components of the closed system of the tray. FIG. 4A shows a filter device comprising hollow fibers in a filter housing, FIG. 4B shows a filter device comprising housing-less hollow fibers in a straight arrangement in a bag, and FIG. 4C shows a filter device comprising housing-less hollow fibers in a u-shape arrangement in a bag;

FIG. 5A is an exploded perspective view of an embodiment of the functionally closed system of the tray of the invention; FIG. 5B is a perspective view of the system of the tray of FIG. 5A; and FIG. 5C is a perspective view of the underside and side of the tray of FIG. 5A;

FIG. 6A is a perspective view of an embodiment of an unloaded cassette of the system, and FIG. 6B is an exploded perspective view of the cassette of FIG. 6A loaded with the functionally closed system of the tray shown in FIG. 5A;

FIG. 7 is a schematic partial view of the system of the invention showing examples of the loaded cassette shown in FIG. 6B, one fully loaded and another partially loaded into an embodiment of the processing unit of the system;

FIG. 8A is a perspective view of an embodiment of the pump of a processing unit engaging a pump shoe provided in the cassette shown in FIG. 6A, and FIG. 8B is a perspective, enlarged view of the pump shoe of the cassette shown in FIG. 6A;

FIG. 9A is a side view of an embodiment of the multiport diverter of the fluid path subsystem engaging an embodiment of the corresponding mating valve drive unit assembly of the processing unit, FIG. 9B is an exploded perspective view of the engagement substructures of the valve and drive unit of FIG. 9A, FIG. 9C is a side view of the dovetailing features of the mating structures of FIG. 9B; and FIGS. 9D and 9E are schematic, cross-sectional drawings, through the center, showing the rotational engagement action of the mating structures and the gap tolerances to allow for axial misalignment;

FIG. 10A is a graph showing the flow rate relative to the rotational speed in RPMs of the pump head using pump heads with three and four rollers, respectively; and FIGS. 10B and 10C are bar graphs showing the flow rate relative to the tubing (conduit) compression using pumps with three and four rollers at 255 RPMs and 14.5 RPMs, respectively;

FIG. 11A is a perspective, side view of an embodiment of the sensor of the system located near the lowest portion of the processing bag (vessel); and FIG. 11B is a cross-section view of the embodiment shown in FIG. 11A;

FIG. 12A-12C are graphs showing examples of an optical sensor output over time for concentration, red blood cell settling and red blood cell extraction, respectively; and FIG. 13 is a schematic diagram of another embodiment of the functionally closed system of the tray, which also illustrating the position of an embodiment of a pump of the processing unit relative to two of the valves of the functionally closed system of the tray, and the position of an embodiment of the sensor relative to the processing bag.

DETAILED DESCRIPTION

To more clearly and concisely describe and point out the subject matter of the claimed invention, the following definitions are provided for specific terms, which are used in the following description and the appended claims. Throughout the specification, exemplification of specific terms should be considered as non-limiting examples.

As used herein, the term "tray" refers to any object, capable of at least temporarily supporting a plurality of components. The tray may be made of a variety of suitable materials. For example, the tray may be made of cost effective materials suitable for sterilization and single-use disposable products.

As used herein, the term "functionally-closed fluid path subsystem" refers to a plurality of components that make up a closed fluid path that may have inlet and outlet ports, to add or remove fluid or air from the subsystem, without compromising the integrity of the closed fluid path (e.g. to maintain an internally sterile biomedical fluid path), whereby the ports may comprise, for example, filters or membranes (e.g. 0.2 um average pore size) at each port to maintain the sterile integrity when fluids or air is added or removed from the subsystem. The components, depending on a given embodiment, may comprise but are not limited to, one or more conduits, valves (e.g. multiport diverters), vessels, receptacles, and ports.

As used herein, the term "vessel" refers to any object capable of containing a liquid within its confines for at least a temporary period of time having at least one opening or access port.

As used herein, the term "biological material" refers to any material of a biological nature that can be separated (e.g. by aggregation) into submaterials. Non-limiting examples of biological materials include, but are not limited to, whole blood, peripheral blood, cord blood and bone marrow. For example, such blood cell samples can be separated via aggregation and sedimentation/removal of RBCs, while nucleated cells remain in a plasma solution. Nucleated cells comprise WBCs and rare stem cells.

One embodiment of a high-throughput system of the invention for processing biological material generally comprises, a tray that supports a functionally closed fluid path subsystem that comprises a vessel for containing and enabling the biological material to separate into two or more distinct submaterials; one or more receptacles to receive one or more of the submaterials from the vessel; a filtration device; a conduit through which one or more submaterials are transported between the vessel and the filtration device; and a one or more engagement structures, such as but not limited to, valves and/or multiport diverters. The housing or processing unit of the system of this embodiment comprises, a pumping device for moving one or more of the submaterials between the vessel and the filtration device via the conduit; one or more second engagement structure corresponding to the first engagement structures for opening and closing the valves of the subsystem. The closed subsystem may be a sterilized subsystem, which is closed to maintain, not only the integrity of the fluid path, but also the integrity of the internal sterile environment of the fluid path subsystem. The system also comprises a locking mechanism to at least temporarily hold the fluid path subsystem in a fixed position relative to the housing unit; and a control device that automatically turns the pumping device on and off, and controls the valves/multiport diverter, in response to one or more commands. One or more of the embodiments of the systems may also comprise a cassette for supporting the tray in the processing unit. Examples of a cassette that may be used in conjunction with one or more of the embodiments of the system are described in U.S. patent application Ser. No. 12/636,112, entitled Disposable Fluid Path Systems and Methods for Processing Complex Biological Materials, filed on Dec. 11, 2009.

Figure 1:
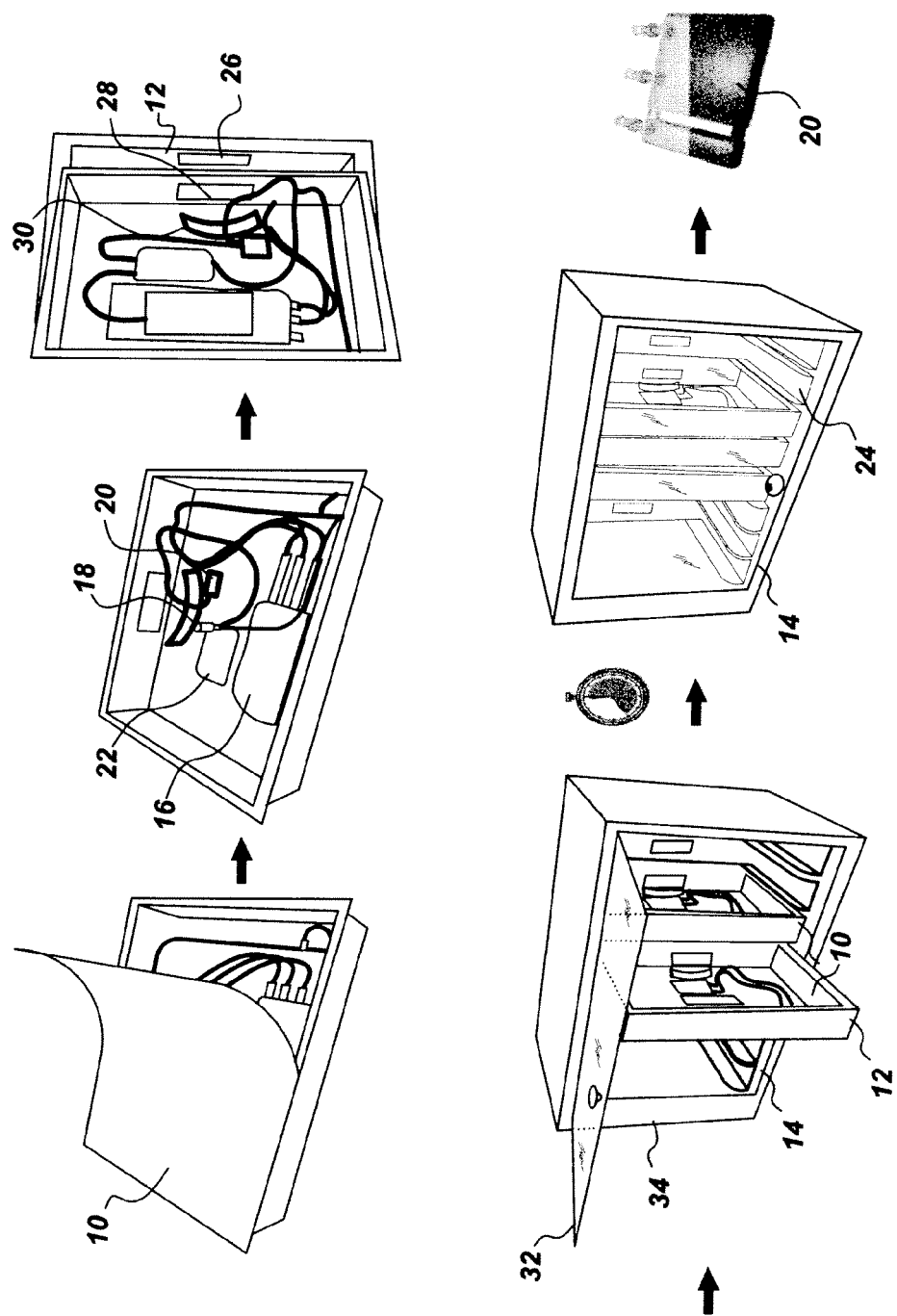
FIG. 1 is a flow diagram for using an embodiment of the system of the invention.

FIG. 1 is a flow diagram of an example of a high-throughput method that uses an embodiment of the system of the invention. The embodiment of the system, generally shown and referred to in FIG. 1 as system 8, comprises tray 10, tray-supporting cassette 12, and processing unit 14. Tray 10 is shown with a functionally closed fluid path subsystem comprising a processing bag 22, tube 18 and a receptacle 20 for capturing and storing, for example, concentrated cellular material. In this example, receptacle 20 is a cryo-container suitable for storing sterile blood materials to be stored cryogenically. As shown in FIG. 1, a removable cover is peeled off of tray 10 to provide access to the inner components of tray 10 which comprise the functionally closed and sterile fluid path subsystem, so that bag 16 containing the biological material to be processed, can be connected to the closed subsystem via a port in the closed subsystem. After bag 16 is connected and placed inside tray 10, tray 10 is placed inside cassette 12. Cassette 12, in this embodiment in part provides structural support for tray 10. Tray 10, in this embodiment, is made from a thin, cost effective material that is suitable for single-use disposable products. Such material may not be structurally strong or consistent enough to ensure tolerances suitable for predictably mating with corresponding structures in processing unit 14. In this embodiment, cassette 12 also enable tray 10 to be loaded in an upright position in processing unit 14.

After placing tray 10 into cassette 12, a cover may be placed over the open side of the cassette and tray, to help maintain the components of the tray. The cassette is than loaded into processing unit 14 comprising a plurality of compartments 24 each with engagement structures that correspond to engagement structures on the tray and/or cassette. Openings 26 and 28 are provided in cassette 12 and tray 10, respectively, through which a pump, (e.g. a peristaltic pump) is able to access and engage shoe 30. Shoe 30 is located, in this embodiment, in tray 10. However, the shoe may be located in the cassette, depending on the type of material from which the tray is made and the configuration of the system.

After the cassette is loaded, and the corresponding engagement structures of the tray/cassette and the processing unit (e.g. automatically by the system) and the corresponding locking structures of the cassette and processing unit (e.g. latch handle and/or alignment assemblies) are engaged, processing of the biomaterials may be initiated by the operator (e.g. by pressing a keypad 34) or automatically by the system once the functionally closed fluid path subsystem is in a fixed and operable arrangement with the pump of the processing unit. The processing unit may also comprise a cover or door 32 to provide security to the system and maintain the cleanliness and integrity of its components. The plurality of compartments 24 may be loaded, and the processing run, synchronously or asynchronously, depending on the system and operating conditions.

The number of compartments and trays for which the system can be fitted, and process asynchronously or otherwise, will depend on the number of operators available, and the efficiency of a given operator, to connect the bag of biological material to the functionally closed subsystem in the tray, load it into the cassette, insert the cassette into the processing unit, and then unload the cassette, remove and store the cryo-bag and dispose of the disposable and tray and its contents.

As a non-limiting example of an embodiment of the system, the system is modular with asynchronous compartments, in which each compartment of the system (compartment loaded with a tray) may be operated independent of the other. The throughput of an asynchronous system, presuming for illustration purposes only, without limiting any embodiments of the methods or systems, that the system will have only a single operator, may be determined by the following equations:

Throughput Entitlement (samples/hr)=60/$T$manual, where $T$manual is the operator load/unload time in minutes   1.

Optimal Channel Count N=ceil[$T$auto/$T$manual]+1, where $T$auto is the automated process time in minutes   2.

Idle time=$T$idle(channel count>=N)=$T$manual*(channel count−1)−$T$auto   3.

Equation 1 indicates that in a multi-channel system, the maximum theoretical throughput is inversely proportional to the hands-on time required by the operator per sample. Specifically, throughput entitlement depends only on the manual operator time and not on automated process time (since time added by the automated process time can be made up by including additional asynchronous processing channels or conversely, if there were an infinite number of parallel asynchronous channels, the throughput would be limited by the number of samples an operator could load unload at any given time).

Equation 2 indicates that the number of asynchronous channels required to reach the entitlement of equation #1 is equal to the ratio of the automated process time per sample divided by the hands on (or manual) time, rounded up to the next whole number (i.e., "ceil" function) plus one. Also, as seen from this equation, reducing the automated process time reduces the number of channels required to reach throughput entitlement and thus system cost (though the process time reduction must be large enough to drop the channel count by 1).

Equation 3 gives the idle time spent by each channel as it awaits manual intervention for a system that has greater than (or equal to) the optimal number of channels given by equation #2. Specifically, as one increases the number or channels beyond the optimal count given by equation #2, the throughput does not increase, it just increases the time spent idle by each processing channel (and also system cost). Having a system with more than an optimal channel count is clearly a sub-optimal solution. For example, with a system having an operator load time of 3 minutes, a total automated processing time of 40 minutes, and an operator unload time of 3 minutes, the system throughput entitlement is 10 samples/hour and the ideal (minimum) number of channels reach this throughput entitlement is N=8.

Otherwise there is not a functional limitation on the number of compartments in the processing unit or the number of trays that can be processed by asynchronous embodiments of the methods and systems that use a manual loading and unloading operation. Depending on the biomaterials to be processed, the methods and systems may be adapted to incorporate automated loading and unloading of the trays, cassettes, and the target retentate receptacle or cryo-bags.

Figure 2:
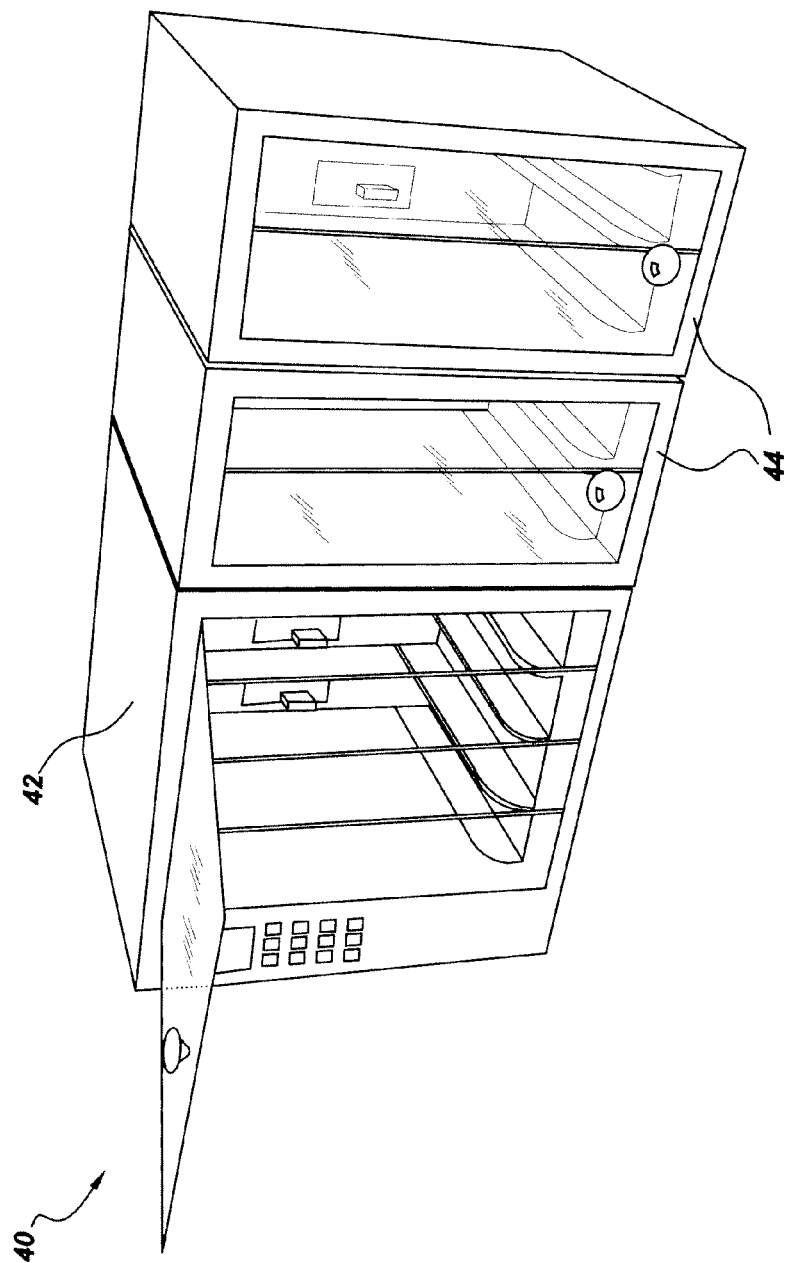
FIG. 2 is a perspective drawing of an embodiment of the processing unit of the invention.

FIG. 2 shows another embodiment of the processing/housing unit generally shown and referred to as unit 40. Unit 40 comprises a main housing 42, as well as two modular housings 44. Such modular subunits may be desired for a variety of reasons including, but not limited to, the cost of an original processing system and an option to scale up in the future, the quantitative needs of the purchaser, the size of the operating space, the number of personnel available to operate the system, and/or to add more subunits that offer optional or upgraded design and functional features.

Figure 3B:
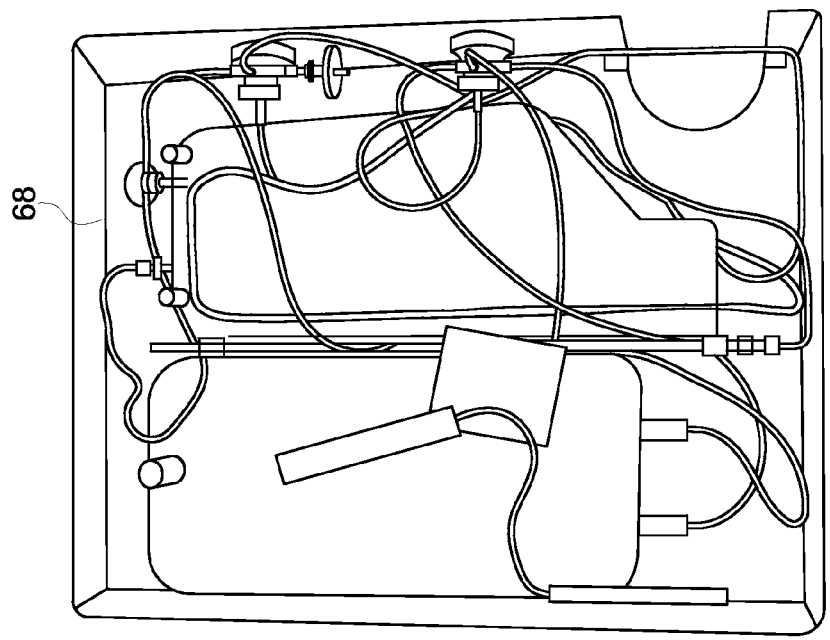
FIGS. 3A and 3B are a perspective drawing and an image, respectively, of embodiments of an empty tray and a tray comprising the functionally closed inner components of the tray.
Figure 3A:
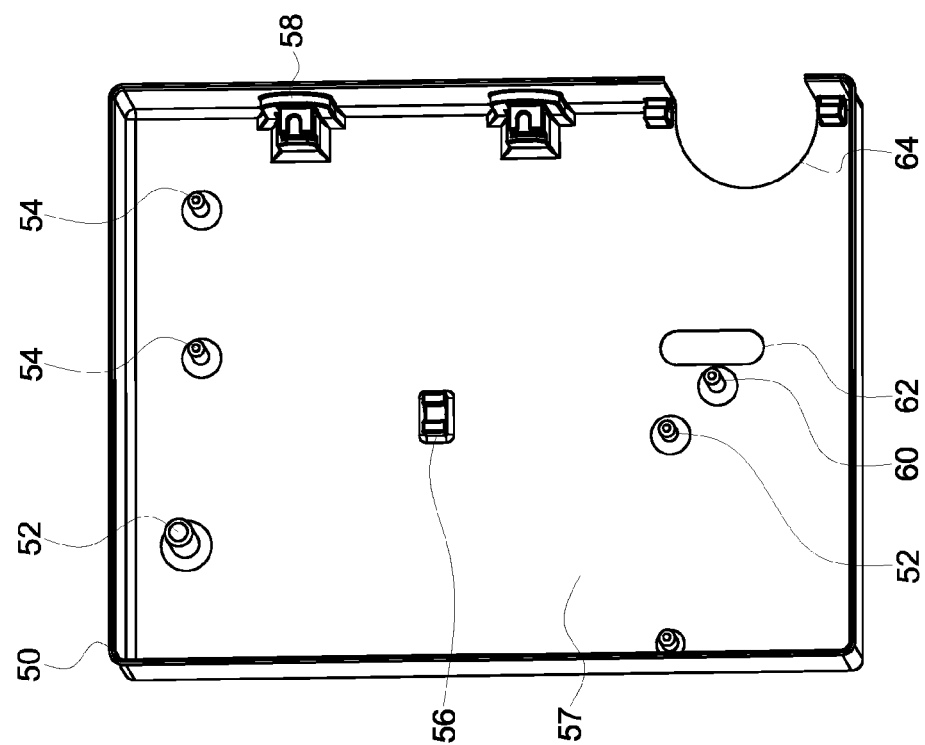

FIGS. 3A and 3B show a drawing and an image, respectively, of an embodiment of an empty tray 50 and a tray 68, which is substantially similar to tray 50 which contains the functionally closed inner components of tray 68 comprising a biomaterial bag, a vessel (processing bag), a filtration device (hollow fiber filter in housing), a receptacle for the target retentate (cryo-bag) and, in this embodiment, a conduit for transporting the biomaterials between the various components of the functionally closed system in the tray.

The tray of the system and the surface features 57 of the tray may be formed by an injection molding process. The embodiment shown as tray 50 comprises a plurality of surface features for holding the components of the functionally closed system in place in the tray which, in this embodiment, comprise pegs 52 corresponding to support holes in the top and bottom of a typical biomaterial bag, pegs 54 corresponding to two support holes in the top of a processing vessel. Peg 60 corresponds to a hole near the bottom of the processing bag and, in this embodiment, positions the very bottom of the processing bag in an opening 62 or window in the tray, and correspondingly in a cassette for the tray, to provide an optical sensor in the processing unit access to the processing bag. Tray 50 further comprises a small channel seat 56 for holding a filter device in a vertical position in the tray, and seats 66 for positioning a portion of the conduit in opening 64 so that is located between a shoe in a cassette for the tray and a pump head located in the processing unit. Tray 50 also comprises, in this embodiment, two mating structures 58 for seating two valves of the functionally closed subsystem that are adapted to mate with corresponding mating structures in the processing unit.

FIGS. 4A-4C show three embodiments of a functionally closed subsystem which differ in these embodiments by the type off filter device incorporated into the functionally closed system of the tray. Each of the figures also shows a pump to illustrate the position of an embodiment of a pump of the processing unit relative to the components of the closed system of the tray, though the pump head, in these embodiments would actually be in the processing unit and not part of the bag set. FIG. 4A shows a filter device 70 comprising hollow fibers in a filter housing (e.g. a TFF), FIG. 4B shows a filter device 74 comprising housing-less hollow fibers in a vertically straight arrangement in a bag, and FIG. 4C shows a filter device 72 comprising housing-less hollow fibers in a u-shape arrangement in a bag.

FIGS. 5A and 5B show another embodiment of the functionally closed fluid path subsystem of the tray, generally shown and referred to as tray 80. In this embodiment, the support pegs are formed in the cassette 88 (FIGS. 6A and 6B), in which tray 80 is to be placed and tray 80 has openings 84 through which the support pegs of cassette are passed when the tray is placed into the cassette. The support pegs of cassette 88 serve a similar purpose as the support pegs in tray 50 shown in FIG. 3A, to support the components of the functionally closed subsystem in tray 80, and are similar passed through the holes provided in the components. FIG. 5C shows the portion of the mating structures 82 of the tray that is located on the outside of the tray, and shows the openings 84 in the bottom of the tray through which the raised surface features (e.g. support pegs) of the trays are formed during, for example, a molding process.

FIG. 6A shows another embodiment of an unloaded cassette 88 of the system, and FIG. 6B shows cassette 88 in an exploded view together with the functionally closed system of the tray 80 shown in FIG. 5A. Cassette 88 comprises a plurality of support pegs 90 that pass through holes in the top of the bag set of tray 80 and support peg 102 that passes through the hole near the bottom of the processing bag to position the lowest most corner of the processing bag in opening 98 that provides an optical sensor in a processing unit access to the processing bag. Cassette 88 also comprises shoe 86 and valve seats 92 for supporting the valve and mating structures in tray 80. Cassette 88 also has openings 94, in the side of the cassette in line with the valve seats 92, through which a component, seated in 114 (FIG. 5B) of tray 80, can be accessed by the processing machine. Cassette 88 also has a cam surface 96 to engage locking mechanisms 105, such as a latch handle on a processing unit to hold cassette 88 in the processing unit in a z direction (axis of cassette insertion) and guides or guiderails 100, which correspond to a channel or rail in the processing unit, to also hold and guide cassette 88 into place as it is inserted into a compartment or channel of the processing unit.

After a tray, such as tray 80, is placed into cassette 88 and a cover (e.g. transparent cover 104) latched into place with latch 106, the tray/cassette subunit is inserted into processing unit. This insertion is illustrated in FIG. 7, which shows one tray/cassette subunit 108 already fully loaded into processing unit 110 and another tray/cassette unit 116 partially loaded into the processing unit of the system. As subunit 116 slides along its guiderails and the corresponding guiderails in processing unit 110, it eventually will engage the second engagement structures 114 of the processing unit with the corresponding engagement structure of the tray/cassette subunit 116. The engagement structures comprise the valve drive assembly.

In parallel, the pump head 112, powered by the motor 113, of the compartment into which subunit 116 is inserted, will engage shoe 118 of subunit 116 impinging a portion of the tubing that is to be placed in tubing path 122 in between the pump head and the shoe, as shown in FIGS. 8A and 8B. In the embodiment shown in FIG. 8A, pump head 112 comprises three contact points (rollers 120), which are located 120 degrees from each other about the perimeter of the circular peristaltic pump head 112. By having the three rollers positioned 120 degrees apart, and wherein the shoe has an arc length that is greater than $0.677*pi*R$, where R is the radius of the contact point path, in this embodiment, this ensures that at any given time during the process, at least one of the rollers is in contact with the conduit (tubing 122) of the functionally closed subsystem in the tray. The compression distance, in this example, (e.g. nominally 2.41 mm [0.095"]) of the pump-loop tubing is set by the relative position of the cassette alignment pins and the pump motor.

In the embodiment shown in FIG. 8A one of two alignment pins, pin 124, is used to properly position the subunit (e.g. 116) within the processing unit. A second alignment pin 128 is shown in FIG. 7. FIG. 8B also shows the alignment feature 126 for seating pin 124 (e.g. together an alignment assembly) to position the cassette in the processing unit. In this embodiment, pins 124 and 126 together align the cassette in the processing unit in the x, y and z axes. Latch handle 105, when engaged with cam surface 96, also serves to fix the cassette in the processing unit in the z direction.

FIGS. 9A through 9E show the details of the engagement between the multiport diverters of the fluid path subsystem and the rotational multiport-diverter drive assembly of the processing unit. FIGS. 9A and 9B show the engagement of a first engagement structure 200 including a disposable bag set stopcock valve with a second engagement structure 206 including the engagement drive head 210 or drive assembly of the processing unit. the valve and the drive are aligned, using the cassette alignment pins, along a plurality of axes. However, because the exact orientation of the stopcock drive tab 212 may vary, the engagement drive head 210 is spring mounted, in this embodiment, on the motor shaft to allow for any tab/drive misalignment. Upon initialization of the drive, the engagement drive head 210 rotates until the slot 214 and tab 212 align, thereupon the spring fully engages the tab and drive head 210 to allow for torque transfer and rotation of the stopcock valve.

FIGS. 9C through 9E show the details of mating structures 220, i.e., a slotted drive head of the mating structure on the processing unit and the mating tab 212 on the mating structure/value of the tray. The embodiment shown in FIGS. 9C through 9E comprises a slot drive configuration with dovetail taper 224. This type of slot drive configuration incorporates a spring loaded slotted drive head and mating tab including a corresponding taper 226 on valve body. The butterfly drive head configuration, shown in FIGS. 9D and 9E, yields maximum surface contact engagement while minimizing any backlash between the mating structures while simultaneously allowing for a sufficient gap between slot and tab to allow for axial engagement. Any backlash is compensated for in part by the control system 230 (e.g. homing feature) and slightly over-damped motions. The tapered dovetail prevents any cam-out during torque transfer. The engagement tolerance in this embodiment, which is non-limiting and for illustration purposes only, is +/−0.011 inches with +/−11.5° of backlash. The mating tab is fixed (e.g. integral with) the valve insert of the functionally closed subsystem in the tray.

As non-limiting examples, FIGS. 10A through 10C illustrate the possible relationship between the tubing type, the rotational speed in RPM of the pump head, the compression of the tubing and the flow rate of materials through the tubing. For example, FIG. 10A is a graph showing the flow rate relative to the rotational speed in RPM of the pump head using pump heads with three and four rollers, respectively; and FIGS. 10B and 10C are bar graphs showing the flow rate relative to the tubing (conduit) compression using pumps with three and four rollers at a speed, 255 RPM, and a low speed 14.5 RPM, respectively.

FIGS. 11A and 11B show the detail of an embodiment of a sensor in position relative to a processing bag of the closed subsystem in a tray. The sensor or sensors may be used to sense, but are not limited to sensing, the presence and concentration of a submaterial at a given location (e.g. height) within the vessel; the environmental conditions within the vessel such as but not limited to, temperature, turbidity, pH, humidity, and pressure; and qualities or characteristics of the biological materials or submaterials. The sensors may be, but are not limited to, optical sensors, ultrasonic sensors, capacitive sensors, piezoelectric sensors, motion sensors, RFID sensors, electromagnetic sensors and load sensors.

The embodiment of the sensor shown in FIGS. 11A and 11B, sensor 132, is located near the lowest portion 134 of the processing bag 130 (vessel). The sensor, such as an optical sensor, may be used for a plurality of process steps. As non-limiting examples, the sensor may be used to, detect the disposable bag set and determine boundary layers of materials in the processing bag (e.g. the RBC/WBC boundary layer and/or the concentrated-fluid/air boundary layer).

One or more of the embodiments comprise an optical sensor that may serve as a single-point volume sensor, when the given boundary layer crosses the sensor, the volume of the material in the processing bag (below the sensor) and the pump loop are known. For example, in systems for processing blood materials, the same trigger level may be used for all blood samples.

Analog output voltage data from the sensor also contains additional information that could be used to verify process operation. More than one optical sensors may be incorporated into the system (e.g. for redundancy). A secondary sensor, for example, may be used to provide four digital signals (using pre-set comparator levels) corresponding to the four states (e.g. no bag, bag present, RBC/WBC boundary layer, concentrated fluid boundary layer). See, for example, the table below.

| Levels | Sensor Output [V] |
|---|---|
| Blood | 0.015 |
| Blood/Dextran | 0.024 |
| RBC | 0.013 |
| WBC/Plasma | 0.450 |
| Concentrate Sample | 0.100 |
| Processing Bag Only | 2.100 |
| No obstruction | 4.000 |

FIG. 12A-12C are graphs of the output of an example of a sensor used in a system for processing blood, showing output over time for concentration, red blood cell settling and red blood cell extraction, respectively.

FIG. 13 is a schematic diagram of another embodiment of the functionally closed system of the tray, illustrating the position of an embodiment of a pump 160 (e.g. peristaltic pump) of the processing unit relative to two of the valves (intake value 148 and filter valve 150) of the functionally closed system of the tray, and the position of an embodiment of the sensor 146 relative to the processing bag 142. The system also comprises a filter device 156, a permeate bag 144 and a supply bag 154. In one or more other embodiments, a supply bag may be a dual use component. For example, once the agent is introduced (transferred from the supply bag) into the processing bag, the partially empty or empty bag can be used as the receptacle for the sedimented material (e.g. RBCs removed from a blood sample). The embodiment shown in FIG. 13 also comprises air filters 158 and 159 and a connecting port 160 for the biomaterial bag.

The system may further comprise an entry device and a display device to enable a user to input information into the system and to access and display information and data about a given process run or a plurality of runs, to compile information and data, and/or to generate reports.

One or more of the embodiments of the system may be used to carry out the high-throughput methods of the invention for processing biological material. For example, one such method generally illustrated in FIG. 1, comprises, a connecting a source containing the biological material to a port in fluid communication with a functionally closed and sterile fluid path subsystem comprising, a first engagement device comprising valves or multi-port diverters, a vessel for containing and enabling the biological material to separate into two or more distinct submaterials, one or more receptacles to receive one or more of the submaterials from the vessel, a filtration device, and a conduit through which one or more submaterials are transported between the vessel and the filtration device, and a tray to support the fluid path subsystem; b) placing the tray in a cassette; c) inserting the cassette into a processing unit comprising, a pumping device for moving one or more of the submaterials between the vessel and the filtration device via the conduit, a drive assembly that interacts with the valves or multi-port diverters; and a second engagement structure corresponding to the first engagement structure, for connecting the drive assembly to the multi-port diverter, and a locking mechanism to at least temporarily hold the cassette in a fixed position relative to the processing unit; d) engaging the first engagement structure with the second engagement structure by inserting the cassette into the processing unit; and e) activating a control device that automatically initiates the pumping device, automatically opens and closes one or more valves in the tray, to cause the biological material to flow through the filtration device, and to cause one or more submaterials to flow into one or more of the receptacles, and automatically stops the pumping device when processing is complete. The method may further comprise, asynchronously repeating steps a) through e) for one or more additional sources of biological materials, connecting each source with a separate additional tray and cassette.

One or more of the embodiments of the system may be adapted to separate the material into aggregated submaterials at least in part based on the relative weight of two or more submaterials. The submaterials separate into sedimentary layers and are drawn off or otherwise extracted from one or more of the sedimentary layers. Once the aggregating agents are mixed with the materials (e.g. whole blood) in the processing vessel, the mixture typically needs time to settle into its various sedimentary layers. For whole blood or cord blood mixed, for example, with Dextran and sodium citrate, settling should occur within 20 minutes.

The methods and system may be used to separate or otherwise process a variety of biological materials. As a non-limiting example, the methods and systems may be used to concentrate nucleated cells from a biological material, such as a sample of blood or bone marrow. For example, such process may comprise the separation and enrichment of nucleated cells, such as, but not limited to, rare stem cells, from cell samples including, but not limited to, blood and bone marrow. The tray may comprise components suited to contact a blood sample with a settling solution, such as a red blood cell aggregating agent (e.g. Dextran) with or without the addition of an enhancing agent (e.g. sodium citrate, sodium succinate). The enhancing agent in this example is added to enhance the RBC sedimentation rate and/or reduce the final RBC packed volume following sedimentation. Subsequently the aggregated RBCs are removed from the upper fraction containing plasma and nucleated cells by drainage, drawing off or other suitable means of transfer. The second step comprises volume reduction and nucleated cell concentration by filtering the RBC-depleted sample. One example of a filtration device that may be used is a hollow-fiber filtration cartridge (General Electric Healthcare, Piscataway, N.J.). Use of the methods or systems to process such cells provides high cell recoveries (e.g. minimal cell trapping), minimal cell damage, and fast processing times. The methods and systems are adaptable for sterile processing of complex biological materials such as but not limited to cord blood and other cell sample materials.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A high-throughput system for processing biological material comprising,
    a tray that supports a functionally-closed fluid path subsystem comprising,
        a vessel for containing and enabling the biological material to separate into two or more distinct submaterials;
        one or more receptacles to receive one or more of the submaterials from the vessel;
        a filtration device;
        a conduit through which one or more submaterials are transported between at least the vessel and the filtration device; and
        a first engagement structure comprising one or more valves, each comprising a mating structure and a plurality of ports in fluid communication with the conduit for selectively directing the material or one or more submaterials between the vessel, the filtration device, and the receptacles;
    a processing unit comprising,
        a pumping device, comprising a pump head and motor, for moving one or more of the submaterials between at least the vessel and the filtration device via the conduit;
        a second engagement structure, comprising a drive head comprising a mating structure that engages the mating structure of the valve,
        a locking mechanism for at least temporarily holding the tray in a fixed position relative to the processing unit;
        a control device, that is in communication with the pumping device that automatically starts and stops the pumping device in response to one or more commands, and that is in communication with the drive head, that opens and closes the ports in response to one or more commands.

2. The system of claim 1, wherein the pumping device comprises a plurality of spaced contact points, at least one of which is in contact with the conduit at any given moment when the pump is in operation.

3. The system of claim 1, further comprising a shoe that corresponds to the pumping device, between which a portion of the conduit is positioned.

4. The system of claim 3, wherein the shoe has a curved surface that corresponds to a curved surface of the pumping device.

5. The system of claim 4, wherein the pumping device comprises a rotating circular component having a perimeter about which the plurality of spaced contact points are located.

6. The system of claim 5, wherein the circular component comprises three contact points which are located substantially equidistant from each other about the perimeter.

7. The system of claim 3, further comprising a cassette adapted to support the tray in a substantially fixed position relative to the processing unit.

8. The system of claim 7, wherein the shoe is located in the cassette.

9. The system of claim 8, wherein the cassette comprises one or more surface features that mate with one or more corresponding surface features in the tray to hold one or more of the tray, the vessel, one or more of the receptacles, the conduit or combinations thereof, in a substantially fixed position relative to the housing unit.

10. The system of claim 9, further comprising a sensor for sensing one or more characteristics of the materials or submaterials.

11. The system of claim 10, wherein at least one of the surface features of the cassette hold at least a portion of the vessel in a position relative to the sensor.

12. The system of claim 10, wherein the sensor is located in a housing unit.

13. The system of claim 10, wherein the sensor determines a location or level of at least one of the submaterials in the vessel.

14. The system of claim 7, wherein the cassette comprises a seat for the first engagement structure of the tray.

15. The system of claim 1, further comprising locking mechanism comprising one or more alignment components that align the tray with the processing unit along an x, y and z axes.

16. The system of claim 15, wherein one or more of the alignment components comprise a pin and corresponding bore.

17. The system of claim 1, wherein the first engagement structure and the second engagement structure comprise corresponding dovetail features.

18. The system of claim 1, wherein the control device is configured to compensate for any backlash between the first engagement structure and the second engagement structure.

19. The system of claim 1, wherein the fluid path subsystem comprises a port configured to mate with an external material source.

20. The system of claim 1, wherein the filtration device is a housingless filter.

21. The system of claim 1, wherein the processing unit comprises a plurality of guides, to support and position a corresponding number of trays in the processing unit.

22. The system of claim 21, comprising a plurality of fluid path subsystems that are configured to operate asynchronously.

23. An automated high-throughput system, for processing biological material, that is adapted to work in conjunction with a functionally closed and sterile subsystem, supported by a tray, comprising, a vessel for containing and enabling the biological material to separate into two or more distinct submaterials, one or more receptacles to receive one or more of the submaterials from the vessel, a filtration device, a conduit through which one or more submaterials are transported between the vessel and the filtration device, and a first engagement structure comprising one or more valves, each comprising a mating structure and a plurality of ports in fluid communication with the conduit for selectively directing the material or one or more submaterials between the vessel, the filtration device, and the receptacles, comprising, a processing unit comprising,
    a pumping device, comprising a pump head and motor, for moving one or more of the submaterials between the vessel and the filtration device via the conduit; and
    a second engagement, comprising a drive head comprising a mating structure that engages the mating structure of the valve,
    a locking mechanism to at least temporarily hold the support structure in a fixed position relative to the processing unit; and
  a control device, that is in communication with the pumping device that automatically starts and stops the pumping device in response to one or more commands, and that is in communication with the drive head, that opens and closes the ports in response to one or more commands.

24. The system of claim 23 wherein the pumping device comprises a plurality of spaced contact points, at least one of which is in contact with the conduit at any given moment when the pump is in operation.

25. The system of claim 23, further comprising a shoe that has a curved surface that corresponds to a curved surface of the pumping device, between which a portion of the conduit is positioned.

26. The system of claim 25, wherein the pumping device comprises a rotating circular component having a perimeter about which a plurality of spaced contact points are located substantially equidistant from each other about the perimeter, at least one of which is in contact with the conduit at any given moment when the pump is in operation.

27. The system of claim 25, further comprising a cassette adapted to support the tray in a substantially fixed position relative to the processing unit.

28. The system of claim 27, wherein the shoe is located in the cassette.

29. The system of claim 23, further comprising a cassette adapted to support the tray in a substantially fixed position relative to the processing unit.

30. The system of claim 29, wherein the cassette comprises one or more surface features that mate with one or more corresponding surface features in the tray to hold one or more of the tray, the vessel, one or more of the receptacles, the conduit or combinations thereof, in a substantially fixed position relative to the processing unit.

31. The system of claim 23, further comprising a sensor configured to sensing one or more characteristics of the materials or submaterials.

32. The system of claim 30, wherein at least one of the surface features of the cassette hold at least a portion of the vessel in a position relative to the sensor.

33. The system of claim 31, wherein the sensor is configured to determines a location or level of at least one of the submaterials in the vessel.

34. The system of claim 29, wherein the cassette comprises a seat for the first engagement structure.

* * * * *